US011583230B2

(12) United States Patent
Lee et al.

(10) Patent No.: US 11,583,230 B2
(45) Date of Patent: Feb. 21, 2023

(54) ELECTRODE PATCH

(71) Applicant: InBody Co., Ltd., Seoul (KR)

(72) Inventors: Kyu Nam Lee, Gyeonggi-do (KR); Ki Chul Cha, Seoul (KR)

(73) Assignee: InBody Co., Ltd., Seoul (KR)

( * ) Notice: Subject to any disclaimer, the term of this patent is extended or adjusted under 35 U.S.C. 154(b) by 279 days.

(21) Appl. No.: 16/893,902

(22) Filed: Jun. 5, 2020

(65) Prior Publication Data

US 2020/0383640 A1 Dec. 10, 2020

(30) Foreign Application Priority Data

Jun. 7, 2019 (KR) .......................... 10-2019-0067477

(51) Int. Cl.
*A61B 6/00* (2006.01)
*A61B 5/00* (2006.01)
*A61B 5/259* (2021.01)
*A61B 5/282* (2021.01)

(52) U.S. Cl.
CPC ............ *A61B 5/6833* (2013.01); *A61B 5/259* (2021.01); *A61B 5/282* (2021.01); *A61B 2562/0209* (2013.01)

(58) Field of Classification Search
CPC ...... A61N 1/0492; A61B 5/6833; A61B 5/282
See application file for complete search history.

(56) References Cited

U.S. PATENT DOCUMENTS

| 4,657,023 | A | | 4/1987 | Kuhn | |
|---|---|---|---|---|---|
| 4,674,512 | A | * | 6/1987 | Rolf | A61B 5/259 600/397 |
| 5,078,139 | A | * | 1/1992 | Strand | A61B 5/259 600/393 |
| 5,255,677 | A | * | 10/1993 | Schaefer | A61B 5/296 607/152 |
| 5,496,363 | A | * | 3/1996 | Burgio | A61N 1/0551 607/148 |
| 5,566,672 | A | * | 10/1996 | Faasse, Jr. | A61N 1/0492 607/152 |
| 5,645,062 | A | * | 7/1997 | Anderson | C09J 9/00 600/391 |
| 5,727,550 | A | * | 3/1998 | Montecalvo | A61B 8/4281 600/386 |

(Continued)

FOREIGN PATENT DOCUMENTS

| JP | 4855734 B2 | 1/2012 |
|---|---|---|
| JP | 2014008166 A | 1/2014 |
| JP | 5759208 B2 | 8/2015 |

*Primary Examiner* — Eun Hwa Kim
(74) *Attorney, Agent, or Firm* — Kolitch Romano Dascenzo Gates LLC

(57) ABSTRACT

An electrode patch is disclosed. The electrode patch includes a substrate of which one surface has an adhesive force and extending in a first direction, a conductive first electrode disposed on one side of the substrate, and a conductive second electrode disposed on another side of the substrate and configured to be electrically separated from the first electrode. The first electrode includes a cut surface extending from a first contact portion contacting a first clamp to an inside of the first electrode, and the second electrode includes a cut surface extending from a second contact portion contacting a second clamp to an inside of the second electrode.

14 Claims, 12 Drawing Sheets

(56) References Cited

U.S. PATENT DOCUMENTS

| | | | | |
|---|---|---|---|---|
| 5,827,184 A | * | 10/1998 | Netherly | A61B 5/25 607/152 |
| 6,912,425 B2 | * | 6/2005 | Nova | A61N 1/04 607/148 |
| 2015/0157225 A1 | * | 6/2015 | Gillberg | A61B 5/6823 600/393 |
| 2017/0095177 A1 | * | 4/2017 | Spencer | A61B 5/332 |

* cited by examiner

ELECTRODE PATCH

TECHNICAL FIELD

Example embodiments relate to an electrode patch, and more particularly, to a disposable electrode patch that is not readily detached from a test subject with improved repeatability.

INTRODUCTION

In related arts, one may need to separately attach a disposable patch-type current electrode and a disposable patch-type voltage electrode, which may cause inconvenience. In addition, the positions of the electrodes to be attached differ from user to user, and thus a distance between the current electrode and the voltage electrode may vary, which may degrade repeatability greatly. Further, the electrodes may be readily detached from the skin due to the weight of a clamp connected to the electrodes and/or an electric wire of the clamp.

SUMMARY

Technical Solutions

According to an example embodiment, there is provided an adhesive electrode patch including a substrate of which one surface has an adhesive force and extending in a first direction, a conductive first electrode disposed on one side of the substrate, and a conductive second electrode disposed on another side of the substrate and configured to be electrically separated from the first electrode. The first electrode may include a cut surface extending from a first contact portion contacting a first clamp to an inside of the first electrode, and the second electrode may include a cut surface extending from a second contact portion contacting a second clamp to an inside of the second electrode.

Each of the cut surfaces of the first electrode and the second electrode may be configured to maintain a contact of a portion of each of the first electrode and the second electrode with a test subject, even when the first electrode or the second electrode is lifted upward by a force greater than the adhesive force.

Each of the cut surfaces of the first electrode and the second electrode may be formed by being cut in the first direction and then being curved and cut at an inner end portion thereof in a direction different from the first direction.

The first electrode may include the first contact portion having a rounded end to be connected to the first clamp. The second electrode may include the second contact portion having a rounded end to be connected to the second clamp.

An end of the cut surface of the first electrode may have a support structure that is curved and cut in a direction approaching the first contact portion from the inside of the first electrode. An end of the cut surface of the second electrode may have a support structure that is curved and cut in a direction approaching the second contact portion from the inside of the second electrode.

Each of the cut surfaces of the first electrode and the second electrode may have a hook-shaped cut structure at an end thereof.

Each of the cut surfaces of the first electrode and the second electrode may include a hole of a preset size at an end thereof.

The substrate may include an indicator configured to guide, between the first electrode and the second electrode, alignment on a specific portion of the test subject.

The indicator may include a cutting line configured to guide the first electrode and the second electrode to be separated from each other.

According to another example embodiment, there is provided an adhesive electrode patch including a substrate of which one surface has an adhesive force and extending in a first direction, a conductive first electrode disposed on one side of the substrate, and a conductive second electrode disposed on another side of the substrate and configured to be electrically separated from the first electrode. The substrate may include an indicator configured to guide, between the first electrode and the second electrode, alignment on a specific portion of a test subject.

The indicator may be associated with a width of the substrate, and a width of a portion of the substrate corresponding to the indicator may be different from that of another portion of the substrate.

The first electrode may include a cut surface extending from a first contact portion contacting a first clamp to an inside of the first electrode. The second electrode may include a cut surface extending from a second contact portion contacting a second clamp to an inside of the second electrode.

The indicator may include a cutting line configured to guide the first electrode and the second electrode to be separated from each other.

According to still another example embodiment, there is provided an adhesive electrode patch including a substrate of which one surface has an adhesive force and extending in a first direction, a conductive first electrode disposed on one side of the substrate, and a conductive second electrode disposed on another side of the substrate and configured to be electrically separated from the first electrode. The substrate may include a cutting line configured to guide, between the first electrode and the second electrode, the first electrode and the second electrode to be separated from each other.

The substrate may include an indicator configured to guide, between the first electrode and the second electrode, alignment on a specific portion of a test subject.

The first electrode may include a cut surface extending from a first contact portion contacting a first clamp to an inside of the first electrode, and the second electrode may include a cut surface extending from a second contact portion contacting a second clamp to an inside of the second electrode.

According to yet another example embodiment, there is provided an adhesive electrode patch including a substrate of which one surface has an adhesive force and extending in a first direction, a conductive first electrode disposed on one side of the substrate, and a conductive second electrode disposed on another side of the substrate and configured to be electrically separated from the first electrode. The substrate may include an indicator configured to guide, between the first electrode and the second electrode, alignment on a specific portion of a test subject.

The indicator may be associated with a width of the substrate, and a width of a portion of the substrate corresponding to the indicator may be different from that of another portion of the substrate.

The first electrode may include a first contact portion that is cut to be connected to a first clamp, and the second electrode may include a second contact portion that is cut to be connected to a second clamp.

The indicator may include a cutting line configured to guide the first electrode and the second electrode to be separated from each other.

According to further another example embodiment, there is provided an adhesive electrode patch including a substrate of which one surface has an adhesive force and extending in a first direction, a conductive first electrode disposed on one side of the substrate, and a conductive second electrode disposed on another side of the substrate and configured to be electrically separated from the first electrode. The first electrode may include a first contact portion that is cut to be connected to a first clamp, and the second electrode may include a second contact portion that is cut to be connected to a second clamp.

Each of respective cut surfaces of the first electrode and the second electrode may be configured to maintain a contact of a portion of each of the first electrode and the second electrode with a test subject, even when the first electrode or the second electrode is lifted upward by a force greater than the adhesive force.

Each of the cut surfaces of the first electrode and the second electrode may be formed by being cut in the first direction and then being curved and cut at an inner end portion thereof in a direction different from the first direction.

An end portion of the first contact portion may have a circular shape having the first electrode as a center and be configured to contact the first clamp. An end portion of the second contact portion may have a circular shape having the second electrode as a center and be configured to contact the second clamp.

Another end portion of the first contact portion may have a support structure that is curved and cut in a direction receding from the first electrode. Another end portion of the second contact portion may have a support structure that is curved and cut in a direction receding from the second electrode.

Each of the support structures of the first contact portion and the second contact portion may have a hooked shape that is cut in a direction different from the first direction.

Each of the other end portions of the first contact portion and the second contact portion may have a support structure including a hole of a preset size at an end of each of the cut surfaces.

The substrate may include an indicator configured to guide, between the first electrode and the second electrode, alignment on a specific portion of the test subject.

The indicator may include a cutting line configured to guide the first electrode and the second electrode to be separated from each other.

According to further another example embodiment, there is provided an adhesive electrode patch including a substrate of which one surface has an adhesive force and extending in a first direction, a conductive first electrode disposed on one side of the substrate, and a conductive second electrode disposed on another side of the substrate and configured to be electrically separated from the first electrode. The substrate may include a cutting line configured to guide, between the first electrode and the second electrode, the first electrode and the second electrode to be separated from each other.

The substrate may include an indicator configured to guide, between the first electrode and the second electrode, alignment on a specific portion of a test subject.

The first electrode may include a first contact portion that is cut to contact a first clamp, and the second electrode may include a second contact portion that is cut to contact a second clamp.

Advantageous Effects

According to an example embodiment, there is provided an electrode patch that is formed by connecting a current electrode and a voltage electrode through a substrate. Thus, it is possible to maintain a distance between measurement points to be consistent and attach the current electrode and the voltage electrode simultaneously by one action, and thus effectively improve repeatability.

According to an example embodiment, there is provided an electrode patch that is attachable to the same position as a position used for the previous measurement of biodata, through an indicator disposed between electrodes. Thus, it is possible to readily improve repeatability.

According to an example embodiment, there is provided an electrode patch having electrodes that are not readily detachable from a test subject through cut surfaces disposed at both ends of the electrodes even when a contact portion is lifted upward by the weight of a clamp and/or a wire connected to the clamp. Thus, it is possible to secure a minimum adhesive portion and minimize a measurement variable. That is, it is possible to effectively prevent the entire electrodes from being detached from the test subject by a force applied to the contact portion.

According to an example embodiment, there is provided an electrode patch in which a first electrode and a second electrode are separable from each other along a cutting line disposed between the first electrode and the second electrode. Thus, it is possible to effectively attach the electrodes to a test subject in any situation.

According to an example embodiment, there is provided an electrode patch that is used as a disposable electrocardiogram (ECG) electrode patch. The electrode patch to be attached to a test subject to measure biodata of the test subject is embodied in a disposable type, and it is thus possible to effectively measure biodata of a test subject sensitive to hygiene.

DETAILED DESCRIPTION

Figure 1:
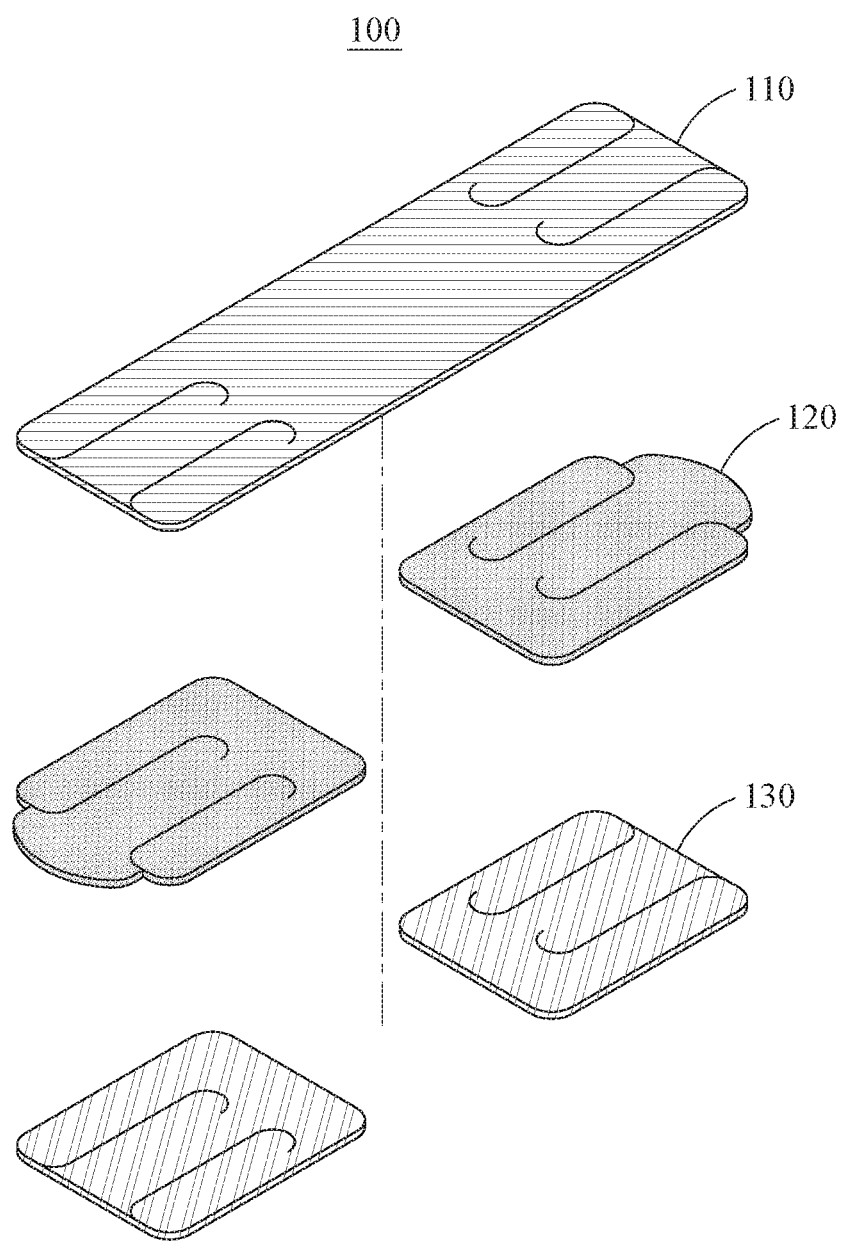
FIG. 1 is a first diagram illustrating an example of an electrode patch according to an example embodiment.

Hereinafter, example embodiments will be described in detail with reference to the accompanying drawings. However, various alterations and modifications may be made to the example embodiments. The example embodiments are not construed as limited to the present disclosure and should be understood to include all changes, equivalents, and replacements within the idea and the technical scope of the disclosure.

The terminology used herein is for describing various examples only and is not to be used to limit the disclosure. Although terms such as "first," "second," and "third" may be used herein to describe various members, components, regions, layers, or sections, these members, components, regions, layers, or sections are not to be limited by these terms. Rather, these terms are only used to distinguish one member, component, region, layer, or section from another member, component, region, layer, or section. Thus, a first member, component, region, layer, or section referred to in examples described herein may also be referred to as a second member, component, region, layer, or section without departing from the teachings of the examples.

Throughout the disclosure, when a component is described as being "connected to," or "coupled to" another component, it may be directly "connected to," or "coupled to" the other component, or there may be one or more other components intervening therebetween.

In addition, the articles "a," "an," and "the" are intended to include the plural forms as well, unless the context clearly indicates otherwise. The terms "comprises," "includes," and "has" specify the presence of stated features, numbers, operations, members, elements, and/or combinations thereof, but do not preclude the presence or addition of one or more other features, numbers, operations, members, elements, and/or combinations thereof.

Unless otherwise defined, all terms, including technical and scientific terms, used herein have the same meaning as commonly understood by one of ordinary skill in the art to which this disclosure pertains and based on an understanding of the disclosure of the present application. Terms, such as those defined in commonly used dictionaries, are to be interpreted as having a meaning that is consistent with their meaning in the context of the relevant art and the disclosure of the present application and are not to be interpreted in an idealized or overly formal sense unless expressly so defined herein.

Hereinafter, example embodiments will be described in detail with reference to the accompanying drawings. Regarding the reference numerals assigned to the elements in the drawings, it should be noted that the same elements will be designated by the same reference numerals, wherever possible, even though they are shown in different drawings. Also, in the description of embodiments, detailed description of well-known related structures or functions will be omitted when it is deemed that such description will cause ambiguous interpretation of the present disclosure.

Figure 2:
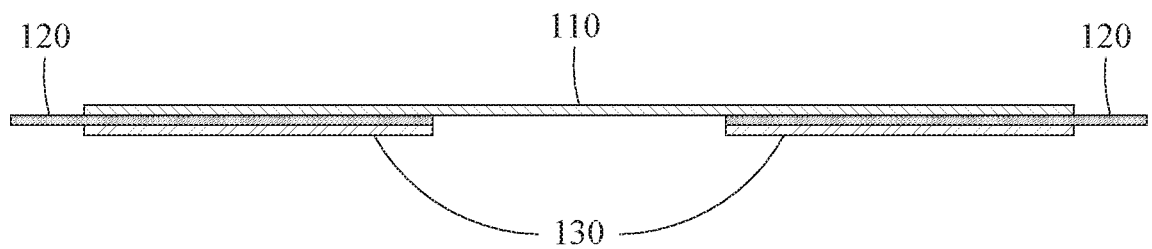
FIG. 2 is a second diagram illustrating the electrode patch of FIG. 1.

FIGS. 1 and 2 are diagrams illustrating an example of an electrode patch according to an example embodiment.

FIG. 1 is an exploded perspective view of an electrode patch 100 according to an example embodiment. The electrode patch 100 includes a substrate 110 and a plurality of electrodes 120, and a plurality of adhesive portions 130. As illustrated in FIG. 1, an upper layer of the electrode patch 100 includes the substrate 110, a middle layer thereof includes the electrodes 120, and a lower layer thereof includes the adhesive portions 130.

According to an example embodiment, the electrode patch 100 may include an electrode configured to apply a current to a test subject and measure a potential difference in a specific portion of the test subject, to measure biodata of the test subject. The term "to measure/measuring" and "measurement" used herein may refer to obtaining a physical quantity or amount using a measuring device or tool. The term "to measure/measuring" and "measurement" used herein may also refer to a process of obtaining a different type of a physical quantity or amount by processing a physical quantity. For example, the process may include processing a physical quantity and obtaining another type of a physical quantity. Thus, the term "to measure/measuring" and "measurement" used herein may encompass a process of applying a current to two points of a body and then obtaining a voltage difference therefrom using a voltmeter, and a further process of calculating an impedance value based on the applied current and the voltage difference.

The biodata of the test subject may be a bioimpedance, or a body composition determined using the bioimpedance. An analysis or measurement of a body composition may refer to analyzing each of elements or components in the test subject or a ratio between the elements or components based on a physical quantity obtained from the test subject. According to an example embodiment, to obtain such a bioimpedance, two current electrodes and two voltage electrodes may be used. For example, one of the current electrodes connected to a current supply device may be attached to a wrist of the test subject, and the other one of the current electrodes may be attached to an ankle of the test subject. In addition, one of the voltage electrodes connected to a voltage measurement device may be attached to the wrist, and the other one of the voltage electrodes may be attached to the ankle. A current may be supplied by the current supply device to the two current electrodes, and a voltage difference between the two voltage electrodes may be measured by the voltage measurement device. Here, a bioimpedance may be determined from the applied current and the measured voltage difference. For example, a simplest way of determining the bioimpedance may be dividing the voltage difference by the current.

The substrate 110 may be provided in a structure that enables the two electrodes 120 to be attached to the test subject at a certain interval. The substrate 110 may extend in a first direction and basically be formed of an insulating material.

The electrodes 120 may be formed of a conductive material, and disposed at both ends of the substrate 110. The electrodes 120 may be used to electrically connect the test subject to the current supply device or the voltage measurement device described above. The substrate 110 connecting the electrodes 120 may be formed of an insulating material, and thus the electrodes 120 may be electrically separated from each other. Although to be described in greater detail, each of the electrodes 120 may have a rounded end, and thus be readily connected to a clamp in any direction. In addition, each electrode may have a hook-shaped inner end portion in a cut surface thereof, and it is thus possible to effectively prevent the entire electrode from being detached from the test subject even though an end of the electrode is lifted upward by a clamp.

The adhesive portions 130 may allow the electrode patch 100 to be attached to the test subject. The adhesive portions 130 may also be disposed at both ends of the substrate 110. They may be basically formed of a conductive material, and thus allow the electrodes 120 and the test subject to be electrically connected to each other. The adhesive portions 130 may also have the cut surfaces corresponding to the electrodes 120.

Through the structure of the substrate 110 in which the two electrodes 120 are attached to the test subject at a certain interval, it is possible to attach the two electrodes 120 simultaneously by one action. In addition, when measuring biodata, a measured value may vary according to a distance or interval between the electrodes 120. However, by readily attaching the electrodes 120 with a certain distance or interval therebetween through the structure described above, it is possible to minimize a variation in the measured value that may be caused by such an electrode attachment interval.

FIG. 2 is a side view of the electrode patch 100 according to an example embodiment.

Figure 3:
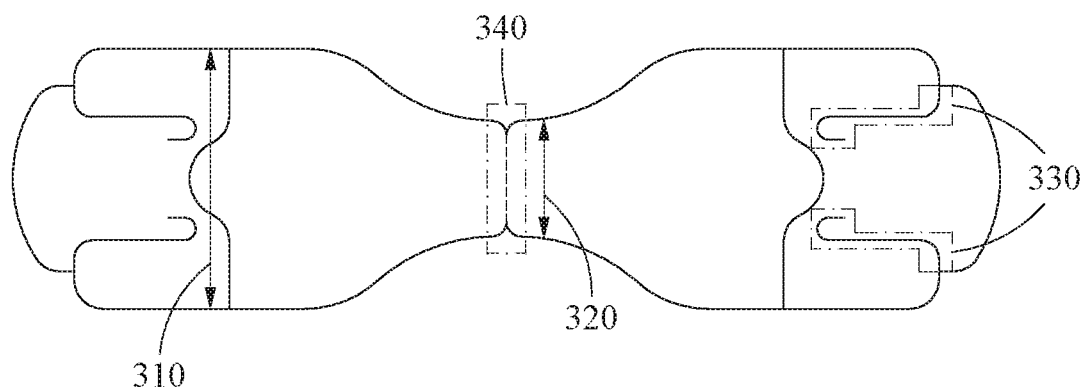
FIG. 3 is a top view of an example of an electrode patch according to an example embodiment.

FIG. 3 is a top view of an example of an electrode patch according to an example embodiment.

Referring to FIG. 3, an electrode patch 300 may be attached to be aligned in a specific portion of a test subject. When repeatedly measuring biodata of the test subject, the electrode patch 300 may be first attached to the test subject and the biodata may be measured therefrom, and then the electrode patch 300 may be detached from the test subject. Afterward, when measuring the biodata of the test subject again, the electrode patch 300 may be attached to the same position as it is attached first to measure the biodata. In general, biodata such as a bioimpedance may vary according to a position of an electrode, and thus the electrode patch 300 may need to be attached to the same position used for the previous measurement to achieve a high level of repeatability. To attach an electrode to the same position, the position may be marked on a body in advance, or the electrode patch 300 may be attached to be aligned in a specific portion of the body that may be used as a reference point or a reference mark, for example, a portion sticking out with a bone.

The specific portion may include an ulnar head and a malleolus, for example. The ulnar head refers to a portion of a wrist in which a bone protrudes, and the malleolus refers to a portion of an ankle in which a bone protrudes. However, examples of the specific portion are not limited to the foregoing examples, and other portions or areas of the test subject may be applied without limitation.

An indicator configured to guide the alignment in the specific portion of the test subject may be included in a substrate. That is, the substrate may include the indicator configured to guide, between a first electrode and a second electrode, the alignment in the specific portion of the test subject. To the indicator, any shape or type that guides the electrode patch 300 to be aligned in the specific portion of the test subject may be applied without limitation. For example, the indicator may be associated with a width of the substrate, and a width of a portion of the substrate corresponding to the indicator may differ from a width of another portion of the substrate. For example, as illustrated, a width 320 of a center portion of the substrate may be designed to be narrower than a width 310 of each of both ends of the substrate at which each electrode is disposed, and that portion may function as the indicator. The width 320 of the center portion of the substrate may be narrower as described above, thereby forming a groove which functions as the indicator. In the groove, a bone protruding in a wrist or an ankle of the test subject may be disposed, thereby improving repeatability. In addition, a cutting line 340 may be used as the indicator, as needed.

In addition, each electrode included in each of both ends of the electrode patch 300 may include a cut surface 330 that extends from a contact portion contacting a clamp to an inside of each electrode. The cut surface 330 included in each electrode may be configured to maintain a contact between a portion of each electrode and the test subject through the cut surface 330 even when the contact portion of each electrode is lifted upward by a force greater than an adhesive force. This will be described in greater detail with reference to FIGS. 5 through 8.

In addition, the electrode patch 300 may include the cutting line 340 configured to guide, between the first electrode and the second electrode, the first electrode and the second electrode to be separated from each other. By readily separating the first electrode and the second electrode included in the electrode patch 300 along the cutting line 340, it is possible to desirably attach the electrodes even when it is difficult to attach the electrode patch 300 all at once. For example, when another medical device is worn on a portion of the test subject in which the electrode patch 300 is to be attached, or when the specific portion of the test subject is amputated, it may not be easy to attach the two electrodes connected to each other through the substrate all at once. In such a case, using the indicator, it is possible to attach the one electrode included in the electrode patch 300 to an accurate position, and separate the other electrode in the electrode patch 300 therefrom along the cutting line 340 and then attach the separated other electrode to a desirable position. Alternatively, using the cutting line 340, it is possible to separate the two electrodes first and then attach them to desirable positions, respectively.

Figure 4:
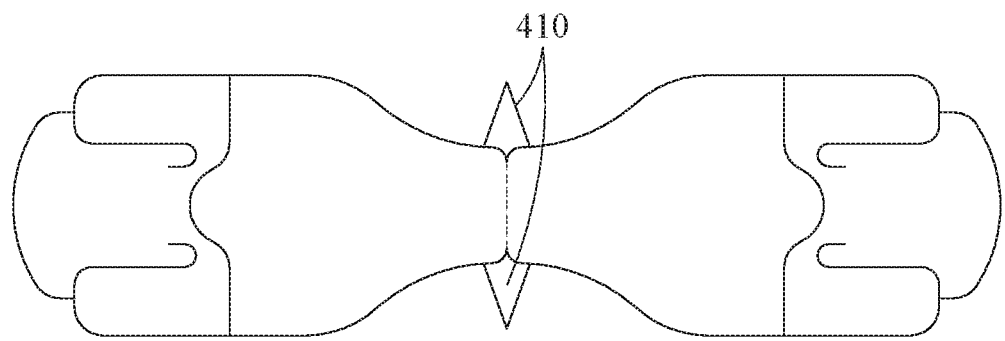
FIG. 4 is a diagram illustrating another example of an electrode patch according to an example embodiment.

FIG. 4 is a diagram illustrating another example of an electrode patch according to another example embodiment.

FIG. 4 illustrates another example of an electrode patch. The electrode patch includes a triangle-shaped indicator 410. The indicator 410 may provide intuitive guidance that enables a specific portion of a test subject to be disposed at end portions thereof.

Figure 5:
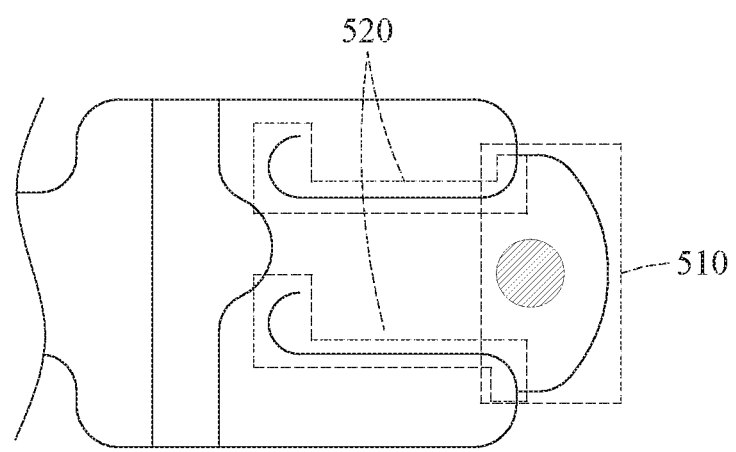
FIG. 5 is a diagram illustrating an example of one side of an electrode patch according to an example embodiment.

FIG. 5 is a diagram illustrating an example of one side of an electrode patch according to an example embodiment.

Referring to FIG. 5, an electrode disposed on one side of an electrode patch has a contact portion 510 having an end with a rounded shape and configured to be connected to a clamp. The clamp may include, for example, tongs and the like to be fastened to the contact portion 510. Here, a cut surface 520 may be configured to maintain a contact between a portion of the electrode and a test subject even when the electrode is lifted upward by a force greater than an adhesive force. For example, as illustrated in FIG. 5, even when a center area between cut surfaces 520 is lifted upward along with the electrode as the electrode is lifted upward by a force greater than an adhesive force, an outer area of the cut surfaces 520 may maintain the contact with the test subject because the force of lifting up the electrode is not directly transferred thereto.

The adhesive portions 130 described above with reference to FIG. 1 may be formed of an adhesive of a silicone material that may not be readily reattached once it is detached after it is attached to the test subject. Thus, when it is detached from the test subject, the electrode patch may need to be replaced with a new one, and thus a cost therefor may increase and repeatability may not be maintained. Thus, to prevent this, a structure of the cut surface 520 may be included in the electrode patch.

The cut surface 520 may be provided in the form that is cut in a first direction (that is, a direction from an end to an inner portion) and then curved at an inner end portion thereof in a direction different from the first direction. That is, the cut surface 520 may have the form that is cut in the first direction from the contact portion 510 toward the inside thereof, and then rotate in the inner end portion and is cut in a second direction (that is, a direction approaching the contact portion 510) opposite to the first direction. An end of the cut surface 520 may be hook-shaped.

The form or shape of the cut surface 520 described above may thus function as a stopper that is configured to prevent the entire electrode from being detached from the test subject.

Figure 6:
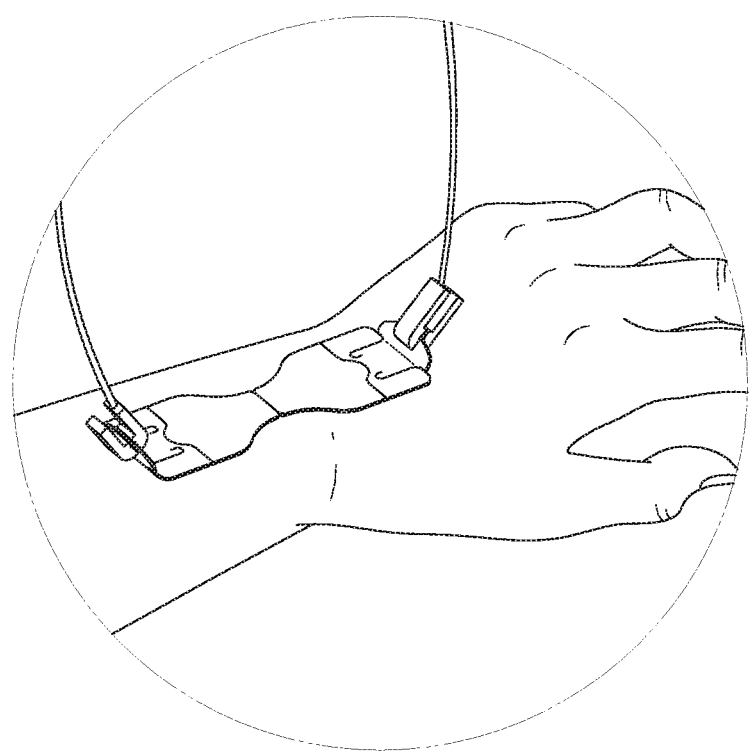
FIG. 6 is a diagram illustrating an example where an electrode patch is attached according to an example embodiment.

FIG. 6 is a diagram illustrating an example where an electrode patch is attached according to an example embodiment.

FIG. 6 illustrates an example where an electrode patch is attached to a wrist of a test subject. In this example, one electrode is for applying a current, and the other electrode is for measuring a voltage.

Figure 7:
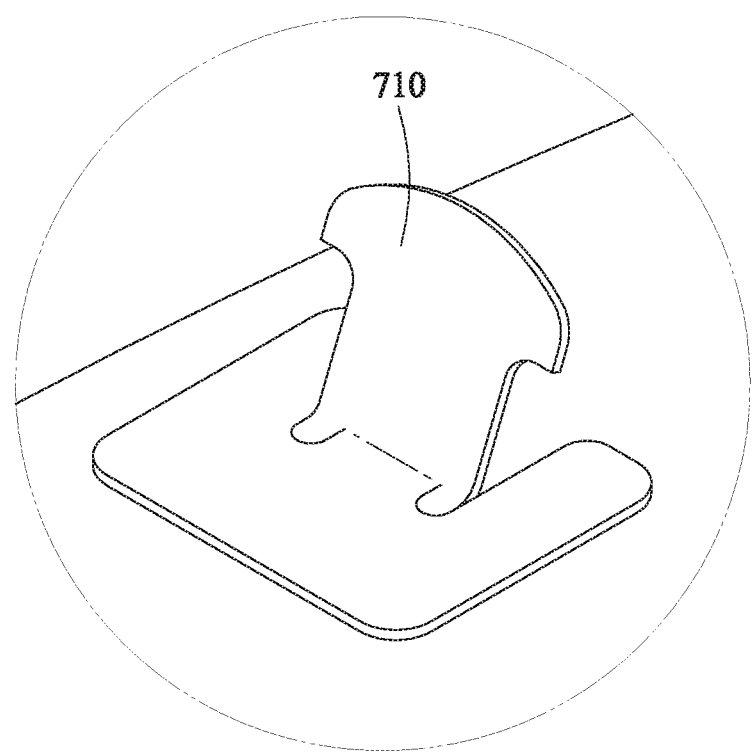
FIG. 7 is a diagram illustrating an example where a contact portion of an electrode patch is lifted uppermost according to an example embodiment.

FIG. 7 is a diagram illustrating an example where a contact portion of an electrode patch is lifted uppermost according to an example embodiment.

Referring to FIG. 7, even when a contact portion 710 is lifted upward maximally, a portion of an electrode may be maintained to be in contact with a test subject through a structure of a cut surface described above. Even though the contact portion 710 is lifted upward due to the weight of a clamp and/or a wire connected to the clamp, it is possible to prevent the entire electrode from being detached from the test subject, and thus secure a minimum adhesive portion and minimize a measurement variable.

Figure 8:
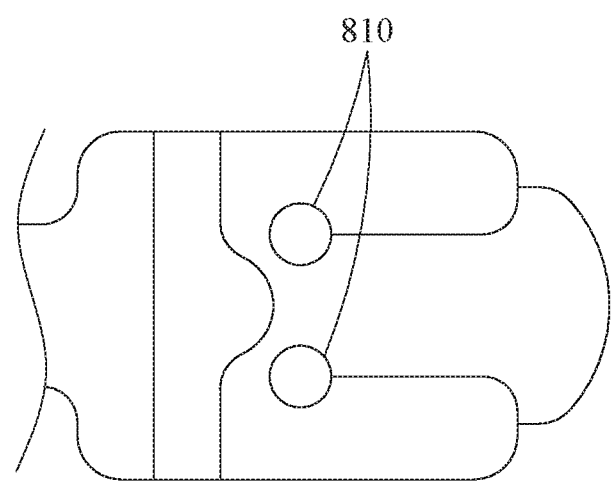
FIG. 8 is a diagram illustrating another example of a cut surface of an electrode patch according to an example embodiment.

FIG. 8 is a diagram illustrating another example of a cut surface of an electrode patch according to an example embodiment.

Referring to FIG. 8, a hole 810 of a preset size may be disposed at an end of a cut surface. In addition to the hook shape described above, various forms or shapes, and/or structures that function as a stopper may be applied without limitation to prevent an entire electrode from being detached from a test subject. Although the hole 810 is illustrated in FIG. 8 as a circular shape for the convenience of description, any forms or shapes, for example, a triangle, a rectangle, a rhombus, a polygon, an ellipse, and the like that function as a stopper to prevent the entire electrode from being detached from the test subject may be applied without limitation.

Figure 9:
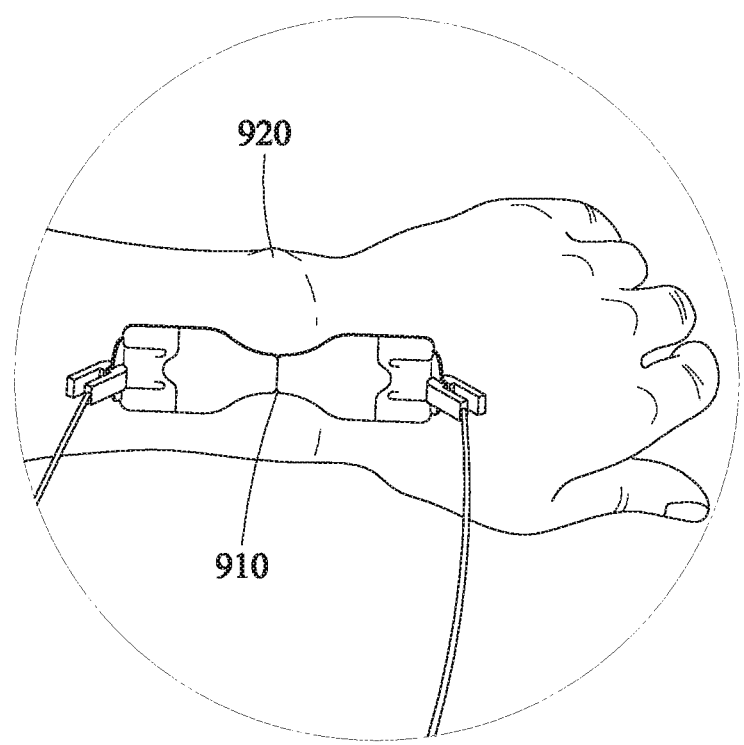
FIG. 9 is a diagram illustrating a first example where an electrode patch is attached according to an example embodiment.
Figure 10:
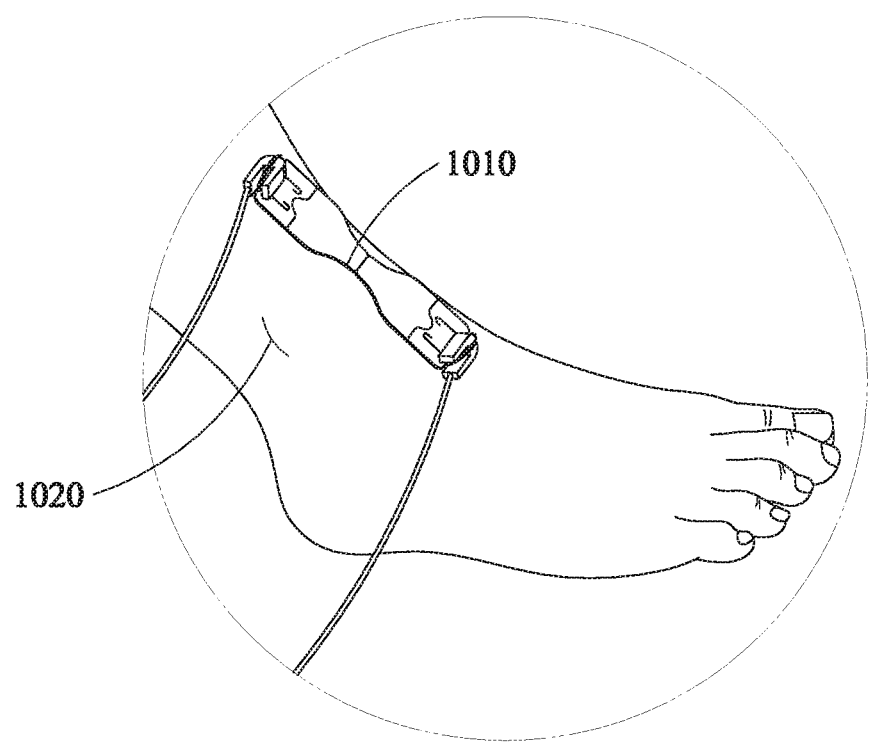
FIG. 10 is a diagram illustrating a second example where an electrode patch is attached according to an example embodiment.

FIGS. 9 and 10 are diagrams illustrating examples where an electrode patch is attached according to an example embodiment.

FIG. 9 illustrates an example where an electrode patch is attached to a wrist of a test subject. In this example, using an indicator 910 of the electrode patch, the electrode patch may be attached to be aligned in an ulnar head 920 of the test subject.

FIG. 10 illustrates an example where an electrode patch is attached to an ankle of a test subject. In this example, using an indicator 1010 of the electrode patch, the electrode patch may be attached to be aligned in a malleolus 1020, or an ankle bone, of the test subject.

FIGS. 11 through 14 are diagrams illustrating examples where an electrode patch is applied according to an example embodiment.

Figure 11:
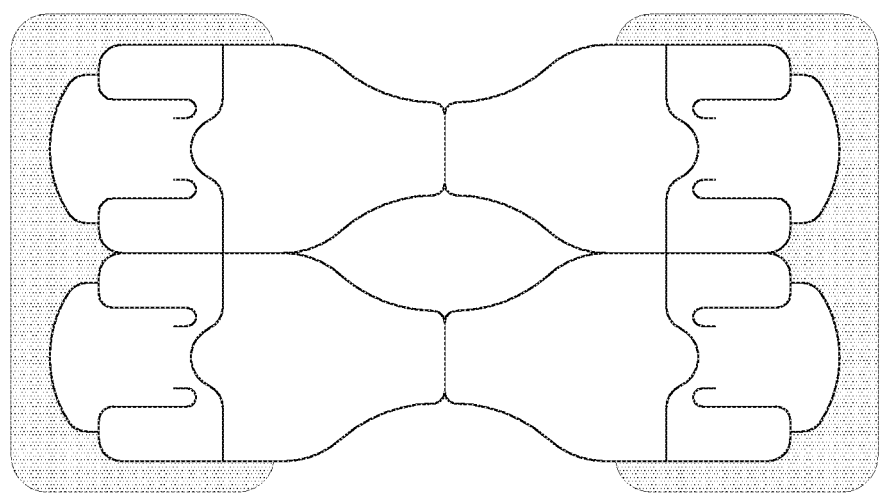
FIG. 11 is a diagram illustrating an example where an electrode patch is applied according to an example embodiment.
Figure 12:
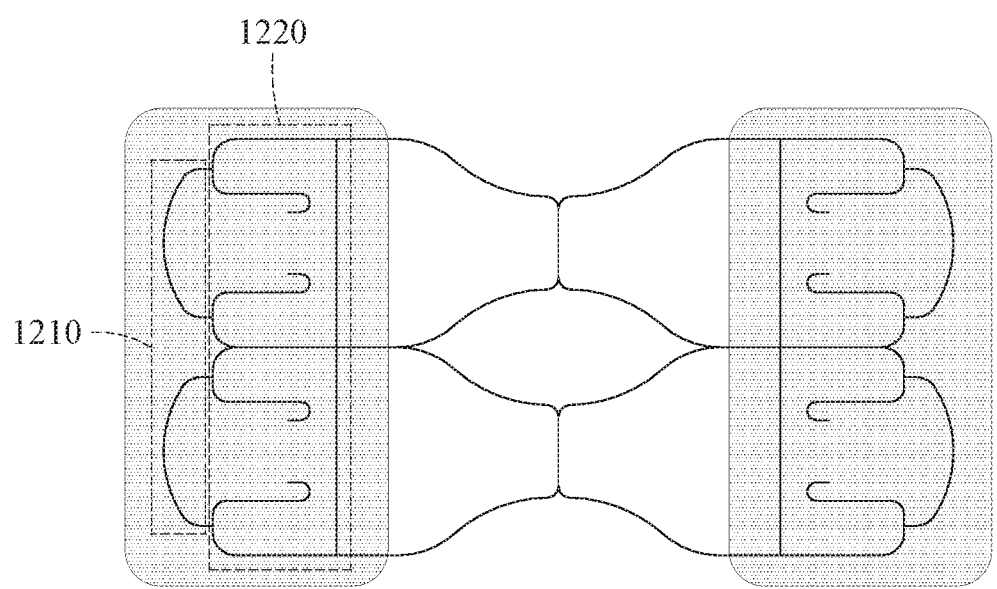
FIG. 12 is a diagram illustrating another example where an electrode patch is applied according to an example embodiment.

FIG. 11 is a front view of a pair of electrode patches according to an example embodiment. FIG. 12 is a rear view of a pair of electrode patches according to an example embodiment. A contact portion 1210 may be a portion to be connected to a clamp, and an adhesive portion 1220 may be a portion having an adhesive force to be attached to a test subject. The contact portion 1210 may have no adhesive force, and thus be readily lifted upward from the test subject to enable the clamp to be fastened.

Figure 13:
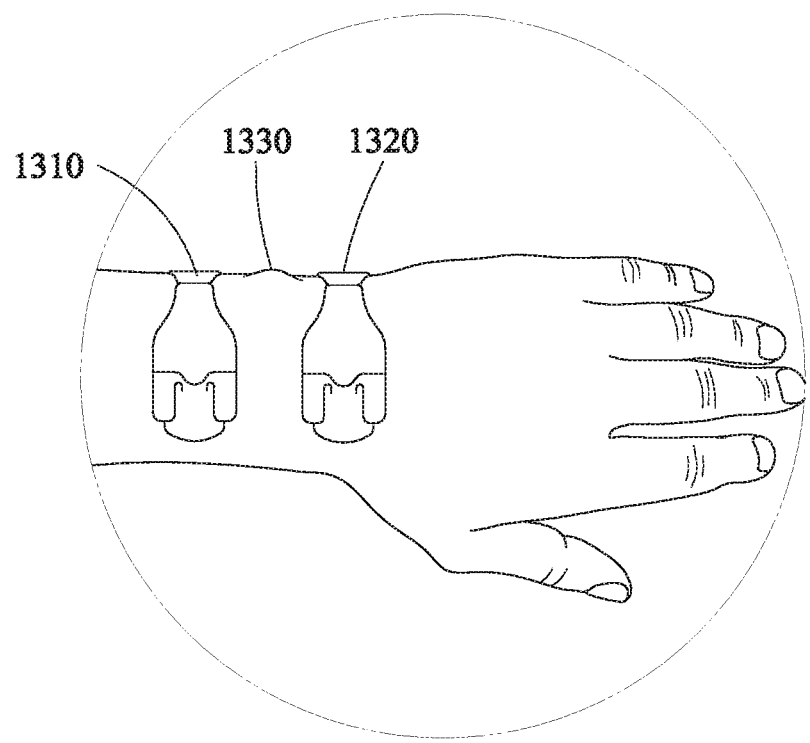
FIG. 13 is a diagram illustrating another example where an electrode patch is applied according to an example embodiment.
Figure 14:
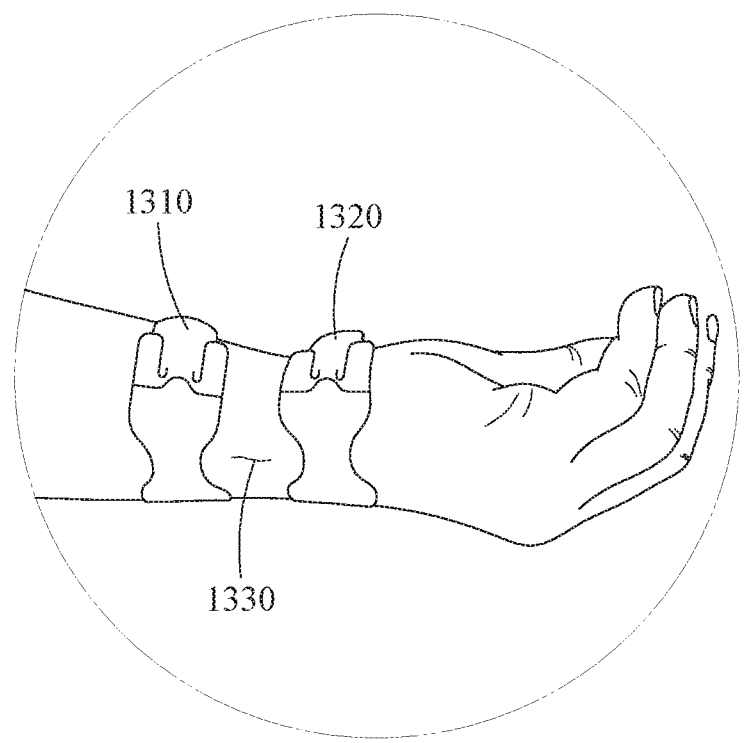
FIG. 14 is a diagram illustrating another example where an electrode patch is applied according to an example embodiment.

According to an example embodiment, a pair of electrode patches may be used to measure a bioimpedance of a test subject, examples of which are illustrated in FIGS. 13 and 14. A pair of electrode patches 1310 and 1320 may be attached such that indicators are aligned to be around an ulnar head 1330.

The units described herein may be implemented using hardware components and software components. For example, the hardware components may include microphones, amplifiers, band-pass filters, audio to digital convertors, non-transitory computer memory and processing devices. A processing device may be implemented using one or more general-purpose or special purpose computers, such as, for example, a processor, a controller and an arithmetic logic unit (ALU), a digital signal processor, a microcomputer, a field programmable gate array (FPGA), a programmable logic unit (PLU), a microprocessor or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a processing device may include multiple processors or a processor and a controller. In addition, different processing configurations are possible, such a parallel processors.

The software may include a computer program, a piece of code, an instruction, or some combination thereof, to independently or collectively instruct or configure the processing device to operate as desired. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion. The software and data may be stored by one or more non-transitory computer readable recording mediums. The non-transitory computer readable recording medium may include any data storage device that can store data which can be thereafter read by a computer system or processing device.

The methods according to the above-described example embodiments may be recorded in non-transitory computer-readable media including program instructions to implement various operations of the above-described example embodiments. The media may also include, alone or in combination with the program instructions, data files, data structures, and the like. The program instructions recorded on the media may be those specially designed and constructed for the purposes of example embodiments, or they may be of the kind well-known and available to those having skill in the computer software arts. Examples of non-transitory computer-readable media include magnetic media such as hard disks, floppy disks, and magnetic tape; optical media such as CD-ROM discs, DVDs, and/or Blue-ray discs; magneto-optical media such as optical discs; and hardware devices that are specially configured to store and perform program instructions, such as read-only memory (ROM), random access memory (RAM), flash memory (e.g., USB flash drives, memory cards, memory sticks, etc.), and the like. Examples of program instructions include both machine code, such as produced by a compiler, and files containing higher level code that may be executed by the computer using an interpreter. The above-described devices may be configured to act as one or more software modules in order to perform the operations of the above-described example embodiments, or vice versa.

The components described in the example embodiments of the present disclosure may be achieved by hardware components including at least one digital signal processor (DSP), a processor, a controller, an application specific integrated circuit (ASIC), a programmable logic element such as a field programmable gate array (FPGA), other electronic devices, and combinations thereof. At least some of the functions or the processes described in the example embodiments of the present disclosure may be achieved by software, and the software may be recorded on a recording medium. The components, the functions, and the processes described in the example embodiments of the present disclosure may be achieved by a combination of hardware and software.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

The invention claimed is:

1. An adhesive electrode patch comprising:
a continuous insulating substrate having a longitudinal axis;
a first conductive electrode disposed on a first end portion of the substrate, and a second conductive electrode disposed on an opposing second end portion of the substrate, wherein the first and second conductive electrodes are spaced apart along the axis;
a first adhesive layer disposed on the first conductive electrode, and a second adhesive layer disposed on the second conductive electrode, such that the first and second electrodes are each sandwiched between the substrate and the respective adhesive layer;
wherein the first and second electrodes each include a respective contact portion protruding beyond the substrate and the respective adhesive layer, such that each contact portion is uninsulated; and
wherein a respective pivotable tab is formed at each end portion of the substrate by a pair of spaced apart cuts passing through the respective substrate, the respective electrode, and the respective adhesive layer, each pivotable tab including the respective contact portion.

2. The electrode patch of claim 1, wherein the pivotable tabs of the first and second electrodes are each configured to maintain a contact between a portion of each of the first and second electrodes and a test subject, including when the first or second electrode is lifted upward by a force greater than an adhesive force of the first or second adhesive layers.

3. The electrode patch of claim 1, wherein each pair of spaced apart cuts includes a first portion extending away from the respective contact portion and a second portion extending toward the respective contact portion.

4. The electrode patch of claim 1, wherein the contact portions are each rounded and configured to be contacted by a clamp.

5. The electrode patch of claim 1, wherein paths of the spaced apart cuts of the first electrode generally extend in parallel and end in a respective hook shape.

6. The electrode patch of claim 5, wherein the respective hook shapes extend in opposite directions.

7. The electrode patch of claim 1, wherein paths of the spaced apart cuts of the first electrode generally extend in parallel and end in an aperture.

8. The electrode patch of claim 1, wherein the substrate comprises an indicator disposed between the first and second electrodes, wherein the indicator is configured to guide alignment for placement on a portion of a test subject.

9. The electrode patch of claim 8, wherein the indicator comprises a cutting line disposed between the first and second electrodes, the cutting line configured to guide a separation of the first and second electrodes.

10. An adhesive electrode patch comprising:
a continuous insulating substrate having a longitudinal axis;
a first conductive electrode disposed on a first end portion of the substrate, and a second conductive electrode disposed on an opposing second end portion of the substrate, wherein the first and second conductive electrodes are spaced apart along the longitudinal axis; and
a first adhesive layer disposed on the first conductive electrode, and a second adhesive layer disposed on the second conductive electrode, such that each of the first and second electrodes is sandwiched between the substrate and the respective adhesive layer;
wherein the first and second electrodes each include a respective contact portion protruding beyond the substrate and the respective adhesive layer, such that each contact portion is uninsulated;
wherein a pair of spaced apart cuts passing through the respective substrate, the respective electrode, and the respective adhesive layer form a respective pivotable tab at each end portion of the substrate, such that each pivotable tab includes the respective contact portion; and
wherein the substrate comprises an indicator disposed between the first and second electrodes and configured to guide alignment for placement on a portion of a test subject.

11. The electrode patch of claim 10, wherein a width of the substrate at the indicator is different than at another portion of the substrate.

12. The electrode patch of claim 10, wherein the indicator comprises a cutting line disposed between the first and second electrodes and configured to guide a separation of the first and second electrodes.

13. An adhesive electrode patch comprising:
- a continuous insulating substrate having a longitudinal axis;
- a first conductive electrode disposed on a first end portion of the substrate, and a second conductive electrode disposed on an opposing second end portion of the substrate, wherein the first and second conductive electrodes are spaced apart along the longitudinal axis; and
- a first adhesive layer disposed on the first conductive electrode, and a second adhesive layer disposed on the second conductive electrode, such that each of the first and second electrodes is sandwiched between the substrate and the respective adhesive layer;
- wherein the first and second electrodes each include a respective contact portion protruding beyond the substrate and the respective adhesive layer, such that each contact portion is uninsulated;
- wherein a pair of spaced apart cuts passing through the respective substrate, the respective electrode, and the respective adhesive layer form a respective pivotable tab at each end portion of the substrate, such that each pivotable tab includes the respective contact portion; and
- wherein the substrate comprises a cutting line disposed between the first and second electrodes and configured to guide a separation of the first and second electrodes.

14. The electrode patch of claim 13, wherein the substrate comprises an indicator disposed between the first and second electrodes and configured to guide alignment for placement on a portion of a test subject.

* * * * *